(12) United States Patent
Demeneix et al.

(10) Patent No.: US 7,795,031 B2
(45) Date of Patent: Sep. 14, 2010

(54) USE OF A NUCLEIC ACID/PEI COMPLEX

(75) Inventors: Barbara Demeneix, Paris (FR);
Grégory Lemkine, Vincennes (FR);
Giovanni Levi, Paris (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 0 days.

(21) Appl. No.: 10/381,185

(22) PCT Filed: Sep. 21, 2001

(86) PCT No.: PCT/FR01/02952
§ 371 (c)(1),
(2), (4) Date: Aug. 28, 2003

(87) PCT Pub. No.: WO02/24231
PCT Pub. Date: Mar. 28, 2002

(65) Prior Publication Data
US 2005/0101552 A1 May 12, 2005

(30) Foreign Application Priority Data
Sep. 22, 2000 (FR) .................................. 00 12126

(51) Int. Cl.
C12N 15/00 (2006.01)
A01K 67/027 (2006.01)
A01K 67/00 (2006.01)

(52) U.S. Cl. .......................... 435/455; 800/8; 800/14; 800/18

(58) Field of Classification Search ................... 800/8, 800/14, 18; 514/44 R; 435/455
See application file for complete search history.

(56) References Cited

U.S. PATENT DOCUMENTS

| 5,945,400 | A | 8/1999 | Scherman et al. | 514/13 |
| 6,013,240 | A | 1/2000 | Behr et al. | 424/1.21 |
| 6,153,597 | A | 11/2000 | Blanche et al. | 514/44 |
| 6,200,956 | B1 | 3/2001 | Scherman et al. | 514/13 |
| 2001/0005717 | A1 | 6/2001 | Wagner et al. | 514/44 |

FOREIGN PATENT DOCUMENTS

| WO | WO 96/02655 | 2/1996 |
| WO | WO 96/25508 | 8/1996 |
| WO | WO 97/12051 | 4/1997 |
| WO | WO 98/46273 | 10/1998 |
| WO | WO 98/59064 | 12/1998 |
| WO | WO 00/03694 | 1/2000 |
| WO | WO 00/69257 | 11/2000 |

OTHER PUBLICATIONS

Remy J, Gene transfer with lipospermines and polyethylenimines, 1998, Adv. Drug Delivery Reviews, vol. 30, pp. 85-95.*
Ghoula D, Size diffusibility and transfection performance of linear PEI/DNA complexes in the mouse central nervous system, 1998, Gene Therapy, vol. 5, pp. 712-717.*
Abdallah B, A powerful nonviral vector for in vivo gene transfer into the adult mammalian brain: polyethylenimine, 1996, Human Gene Therapy, vol. 7, pp. 1947-1954.*
Ghoula D, Size diffusibility and transfection performance of linear PEI/DNA complexes in the mouse central nervous system, 1998, Gene Therapy, vol. 5, pp. 712-717.*
Abdallah B, A powerful nonviral vector for in vivo gene transfer into the adult mammalian brain: polyethylenimine, 1996, Human Gene Therapy, vol. 7, pp. 1947-1954.*
Johansson CB, Neural Stem Cells of the Adult Human Brain, 1999, Experimental Cell Res., vol. 253, pp. 733-736.*
Boussif et al: "A versatile vector for gene and oligonucleotide transfer into cells in culture and in vivo: Polyethylenimine"; Proc. Natl. Acad. Sci. USA, vol. 92, pp. 7297-7301, Aug. 1995, XP-002171011.
Goula et al: "Size, diffusibility and transfection performance of linear PEI/DNA complexes in the mouse central nervous system"; Gene Therapy (1998) 5, 712-717, XP-001009995.
Demeneix et al: "Optimizing Polyethylenimine-Based Gene Transfer into Mammalian Brain for Analysis of Promoter Regulation and Protein Function"; Methods in Molecular Biology, vol. 133: Gene Targeting Protocols, 21-35, XP-001010012.
Fischer et al: "A Novel Non-Viral Vector for DNA Delivery Based on Low Molecular Weight, Branched Polyethylenimine: Effect of Molecular Weight on Transfection Efficiency and Cytotoxicity"; Pharmaceutical Research (1999), 16(8), 1273-1279, XP-001010014.
Abdallah et al: "Non-viral gene transfer: Applications in developmental biology and gene therapy"; Biol. Cell (1995) 85, 1-7, XP001010029.
Abdallah et al: "A Powerful Nonviral Vector for In Vivo Gene Transfer into the Adult Mammalian Brain: Polyethylenimine"; Human Gene Therapy 7 (16), 1947-1954 (Oct. 1996), XP-001010019.
Lemkine et al: "Optimisation of Polyethylenimine-Based Gene Delivery to Mouse Brain"; Journal of Drug Targeting, 1999, 7(4), 305-12, XP-001010011.
Horbinski et al: "Polyethyleneimine (PEI)-mediated transfection of sympathetic neurons in vitro"; Society for Neuroscience Abstracts, (1999) vol. 25, No. 1-2, pp. 2003, Meeting Info: 29th Annual Meeting of the Society for Neuroscience, Miami Beach, Florida, USA, Oct. 23-28, 1999, XP-001010028.
Ouatas et al: "T3-dependent physiological regulation of transcription in the Xenopus tadpole brain studied by polyethylenimine based in vivo gene transfer"; Chemical Abstracts, 131:40294, Int. J. Dev. Biol. (1998), 42(8), 1159-1164, XP-002186320.
Intercellular trafficking activity of herpes simplex virus US11 gene product in the mouse brain, Mori et al., Molecular Brain Research, 2005, pp. 158-163.

* cited by examiner

Primary Examiner—Peter Paras, Jr.
Assistant Examiner—David Montanari
(74) Attorney, Agent, or Firm—Steptoe & Johnson LLP

(57) ABSTRACT

The invention concerns the use of a nucleic acid/cationic polymer complex, preferably polyethyleneimine (PEI) for preparing a composition for intraventricular stereotactic screening of stem cells of the brain for preparing a medicine for treating neurodegenerative and/or demyelinating disease. The invention further concerns a method for obtaining an animal whereof the genome of stem cells of the brain are modified by using said complex. The invention also concerns a method for obtaining an animal for screening compounds designed to modify the disposition of stem cells of the brain.

13 Claims, 7 Drawing Sheets
(2 of 7 Drawing Sheet(s) Filed in Color)

Figure 1:
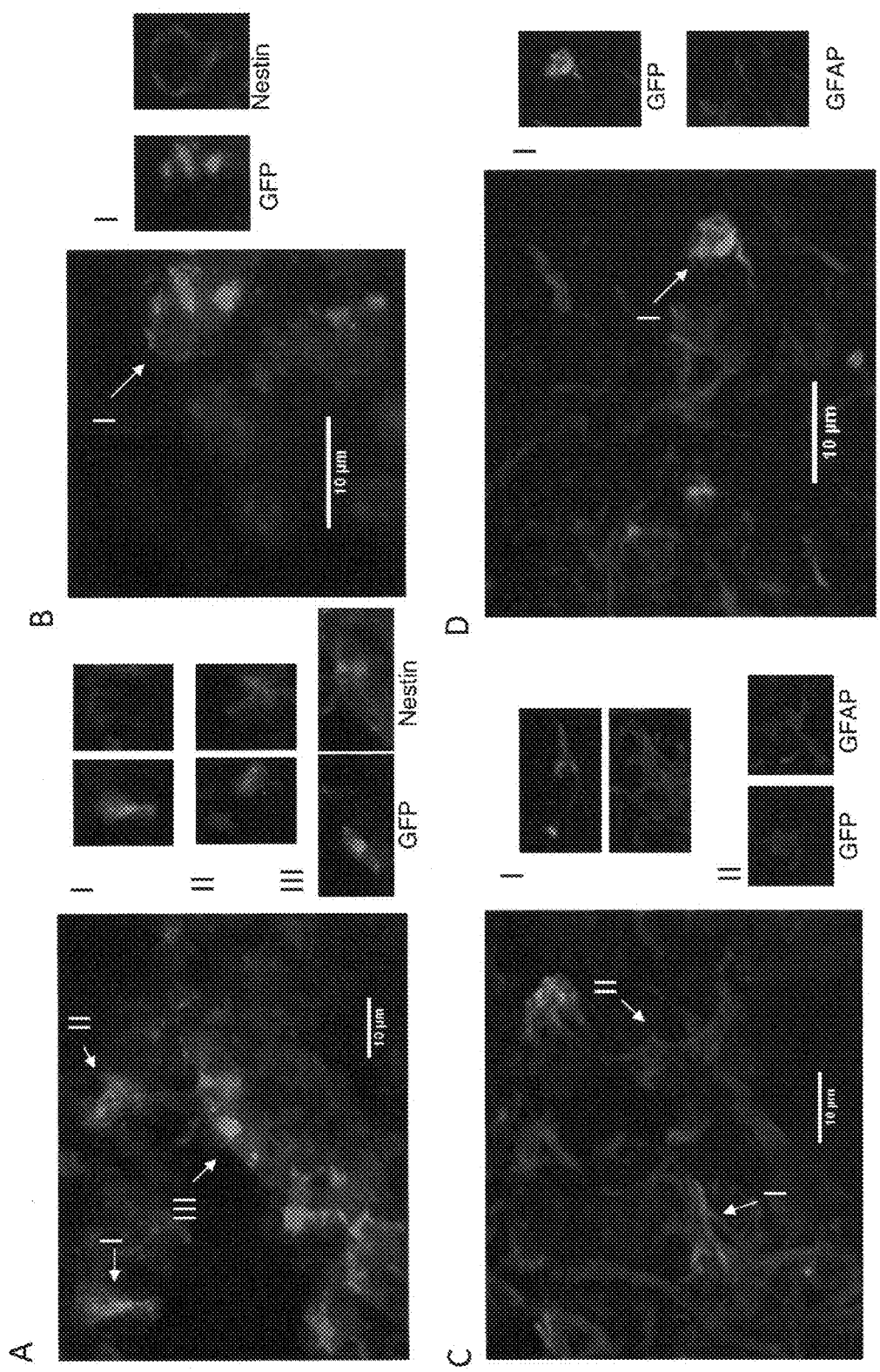

Fig 1. Use of reporter plasmid encoding Green fluorescent protein (GFP) complexed at different concentrations with PEI shows targeting of the neural stem cell population.

USE OF A NUCLEIC ACID/PEI COMPLEX

The present invention relates to biology, and more particularly to gene therapy. The present invention relates to a novel use of a nucleic acid/cationic polymer, and in particular nucleic acid/polyethyleneimine, complex for preparing a composition intended for the targeting of stem cells of the brain. Such a composition is particularly intended for the preparation of a medicinal product intended for the treatment of neurodegenerative and/or demyelinating diseases. The invention also relates to a method of producing an animal, with the exception of humans, in which at least one stem cell of the brain has undergone an event of site-specific recombination targeted to a DNA sequence of interest. The invention also relates to the animal which can be obtained using the method.

Neurodegenerative diseases constitute a major and increasing problem for public health among the aging population. For this reason, a great deal of effort is currently directed toward the development of protocols for transferring genes into the brain. Such protocols are difficult to develop because they require, inter alia, having effective and safe transfer vectors, and they require the difficulties specific to delivering DNA into the brain to be overcome, namely the existence of the blood-brain barrier, which aims to prevent vascular delivery of the vectors, and the post-mitotic state of the neuronal population.

With regard to transfer vectors, significant success in delivering DNA into the mature brain has been obtained with experimental approaches using direct injection of viral vectors based on DNA viruses such as adenoviruses (Akli et al., 1994; Bajocchi et al., 1993; Davidson et al., 1993; Le Gal La Salle, et al., 1993), the vectors derived from the herpes virus (Boviatsis et al., 1994; Pakzaban et al., 1994; Wood et al., 1994) and adenovirus-associated viruses (AAV) (Kaplitt et al., 1994). More recently, a retroviral system based on the human immunodeficiency virus (HIV) has been used to mediate the stable transduction of neurons in the rat brain (Naldini et al., 1996).

Although efforts are mainly directed toward viral vectors, nonviral techniques constitute varied alternatives full of potential. Specifically, chemical transporters of DNA have many advantages over viral vectors. Their use provides greater flexibility, and they are simpler to prepare, to purify and to store. Safety data and toxicity data are also easier to obtain. They can be used with any sort of DNA, thus allowing the use of long nucleic acid sequences, such as a whole gene, associated with plasmidic vectors.

Among the nonviral vectors, two main classes of molecules can be distinguished overall: cation lipids, such as DOGS (diocade cylamidoglycyl spermine) or Transfectam® (Behr et al., 1989) or Lipofectin® (Felgner et al., 1987), and DNA-binding polymeric cations, such as poly-L-Lysine (PLL), protamine, "cationized" albumin, polyethyleneimine (PEI) (Boussif et al., 1995), block copolymers (Read et al., 2000; Oupicky et al., 2000; Wolfert et al., 1999), and polyamidoamine dendrimers (Tang et al., 1996; Planck et al., 1999).

The use of cationic polymers, and in particular of PEI, for delivering genes in vivo has shown that these vectors can provide high levels of expression in the brain (Abdallah et al., 1996; Boussif et al., 1995; Goula et al., 1998; Lemkine et al., 1999).

In order to bypass the difficulty constituted by the "blood-brain" barrier, other routes of administration have been developed, such as direct injection of virus, such as the attenuated herpes simplex virus (Chambers et al., 1995) or sterotactic injection, such as injection of DNA/PEI complex (Abdallah et al., 1996). Another possible route of administration consists of the local production of therapeutic peptide or protein; thus, cell lines transformed with retroviruses have been used to produce therapeutic proteins in order to correct lysomsomal disease affecting the brain (Snyder et al., 1995) and brain tumors have been treated with cells producing retroviruses (Culver et al., 1992; Barba et al., 1994).

The third major obstacle to the delivery of DNA in the CNS, consisting of the post-mitotic state of the vast majority of neuronal cells, represents, to date, an obstacle which is difficult to overcome.

The present invention therefore proposes to solve this problem by specifically targeting the cells of the central nervous system (CNS) which have conserved their ability to divide and to differentiate. Specifically, cells which correspond to neuronal stem cells have recently been demonstrated in vivo using retroviruses, or using a marker such as thymidine or bromodesoxyuridine (BrdU); since retroviruses integrate only in dividing cells, they make it possible to follow the entire cell descendance, thus reflecting a particular lineage. After several years of studies, two sites have now been recognized as being the main sites of cell proliferation in the adult brain: the subventricular zone and the subgranular zone of the hippocampus dentate gyrus. However, not all the cells of these regions have the proliferative potential of the particular cell subpopulation constituted by the stem cells. The exact phenotype of the most primitive cell in these regions is still poorly understood, but recent articles have shed light on this complex question. Johansson et al., (1999) have provided a demonstration that a subpopulation of ependymal cells bordering the third ventricle are stem cells.

Subsequently, Doetsch et al., (1999) have presented clearer arguments in favor of the idea that the progenitor cells belong to a class of subventricle cells which express the GFAP (Glial Fibrilly Acidic Protein) marker, which indicates that the stem cells would be subependymal astrocytes. Moreover, a third group has shown that, even if these two types of cell were capable of division, only the subependymal astrocytes could renew themselves and give rise to neurons and glial cells (Chiasson et al., 1999). Another marker makes it possible to characterize the progenitor cells of the central nervous system: the protein nestin, which constitutes an intermediate filament of the cytoskeleton (McKay et al., 1997).

It therefore appears to be of major interest to develop a protocol for specifically targeting a transgene into the embryonic stem cells of the adult brain. This is the problem that the present invention proposes to solve. The studies of the prior art, and in particular those of Goula et al., (1998), have not made it possible to achieve this aim. Specifically, the article by Goula et al., (1998), which reports preliminary studies regarding the setting up of the use of PEI in the central nervous system in a general way (i.e. both in the newborn and in the adult) describes a transfection procedure which does not make it possible to specifically target the adult neural cell stem population; the article by Goula et al., (1998) shows that the various main cell types of the brain, i.e. the glial cells and the neurons, are indifferently transfected and express the transgene. Entirely fortuitously, the inventors have solved the problem posed by using a nucleic acid/cationic polymer complex to prepare a composition intended for the targeting of stem cells of the adult brain.

The solving of the technical problem has been obtained by introducing, preferably by injecting, the composition according to the invention into the adult brain, and preferably into one or more ventricles of the brain, close to or into the ventricular stem cells of the brain, preferably of the adult brain. The composition according to the invention is preferably injected into the brain ventricle(s) where the embryonic stem cells of the brain (i.e. the ventricular stem cells of the brain) have been located. Even more preferably, this involves one or more lateral ventricles. In addition, the composition according to the invention can be injected into the 3rd or 4th ventricle and then diffused into the cephalic fluid so as to reach the ventricular embryonic stem cells. The composition according to the invention is introduced, preferably by intraventricular injection into the adult brain, the injection of said composition being carried out stereotactically and said injection lasting at least 10 minutes, optionally at least 15 minutes, or at least 20 minutes.

The solving of the technical problem has also been obtained by using small amounts of nucleic acids and small injection volumes. Specifically, to target the stem cells of the adult mouse brain, the amount of said nucleic acid present in said composition should be at least less than 2.5 µg. Thus, it may be less than 2 µg, than 1.75 µg, than 1.5 µg, than 0.75 µg, than 0.5 µg, than 2.5 µg, than 0.1 µg, than 0.05 µg, or than 0.01 µg. In addition, for the targeting of the stem cells of the adult mouse brain, too large a volume of said composition should not be injected, and it should not under any circumstances exceed 5 µl, since larger volumes lead to a reflux at the time of injection and are liable to cause damage to the tissues. Thus, the volume of composition injected into the adult mouse brain is less than 5 µl, optionally less than 4 µl, less than 3 µl, less than 2 µl or less than 1 µl.

These various volumes, injection time and amount of nucleic acid present in the composition according to the invention should be adjusted by those skilled in the art when the injection is carried out in an animal other than the mouse. This adjustment is within the scope of those skilled in the art who, without any excessive effort, can rapidly determine the parameters for use of the composition according to the invention for targeting the ventricular embryonic stem cells of an adult brain. They can thus, before proceeding experimentally, determine the volume of the cerebral ventricles and in particular of the lateral ventricles in the mouse and in the target animal (by magnetic resonance imaging for example) and, by a simple rule of three, determine the amount of nucleic acids, the volume and also the injection time necessary to reproduce the results obtained in the mouse. For this reason, the present invention relates to the use of a nucleic acid/cationic polymer complex, for preparing a composition intended for the targeting of ventricular stem cells of the adult brain of an animal, characterized in that the amount of said nucleic acid present in said composition is adjusted as a function of the volume of the cerebral ventricle of said animal and is determined proportionally to the amount used to target the stem cells of the adult mouse brain, the concentration of said nucleic acid present in the ventricle of said animal being less than or equal to that used for the targeting of the stem cells of the adult mouse brain. The present invention also relates to the use of a nucleic acid/cationic polymer complex, for preparing a composition intended for the targeting of ventricular stem cells of the adult brain, characterized in that the volume of said composition is adjusted as a function of the volume of the cerebral ventricle of said animal and is determined proportionally to the volume used to target the stem cells of the adult mouse brain.

The cell targeted with the compound of the present invention is a eukaryotic cell of an animal. Preferably, the animal according to the invention is a vertebrate, more preferably a mammal, preferably chosen from the group composed of mice, rats, rabbits, hamsters, guinea pigs, bovines, members of the goat family, members of the sheep family, horses and primates, including humans. The animal is preferably a human, the stem cell from the brain being a human cell.

According to another preferred embodiment, the animal is a mouse and the stem cell is a murine cell.

The examples and results below demonstrate the favored transfection of adult neural stem cells in particular regions of the brain.

The present invention is not limited only to the targeting of stem cells of the brain, but also to cells of the brain which are not in the post-mitotic state and which are capable of dividing; in this respect, mention may be made of the cells of brain tumors, such as, for example, gliomas or astrocytomas.

According to a preferred embodiment of the invention, said composition is introduced stereotactically. However, any means for delivering the composition of the invention close to or into the stem cells of the brain can be envisioned; in this respect, mention should be made of all the systems for targeting across the blood/brain barrier systemically.

According to a preferred embodiment, said cationic polymer is chosen from the group composed of the polycationic polymers such as polyethyleneimine (PEI), poly-L-lysine, poly-D-lysine, polyamidoamine, polyamine, block copolymers (Read et al., 2000; Oupicky et al., 2000; Wolfert et al., 1999), and polyamidoamine dendrimers (Tang et al., 1996; Plank et al., 1999). Preferably, the polycationic polymer is polyethyleneimine (PEI). Preferably it is low molecular weight PEI, more preferably it is PEI having an average molecular weight of less than or equal to 88 kDa, less than or equal to 44 kDa, less than or equal to 35 kDa, less than or equal to 30 kDa, less than or equal to 22 kDa, or less than or equal to 11 kDa. Even more preferably, the PEI used is a PEI of 22 kDa (EXGÈNE 500®, EUROMETEX Soufflemeyer-sheim, France). Other cationic polymers can optionally be used, such as nucleic acid binding proteins, among which mention should be made of histones, protamine, ornithine, putrescine, spermidine and spermine. In addition, the possibility exists of grafting the cationic polymer with proteins, antibodies or membrane receptor ligands, making it possible to specifically target cells by facilitating internalization of the complexes.

The nucleic acid/cationic polymer complex according to the invention is intended for the preparation of a medicinal product intended for the treatment of neurodegenerative and/or demyelinating diseases. Among these diseases, mention should be made, in a nonexhaustive manner, of diseases such as Alzheimer's disease, Parkinson's disease, Huntington's chorea and multiple sclerosis. The complex according to the invention can also be used to prepare a medicinal product intended to modify the evolution of the stem cells of the brain and/or to increase the survival of the stem cells of the brain.

For the preparation of these medicinal products, said nucleic acid is chosen from single-stranded DNA, double-stranded DNA, single-stranded RNA, double-stranded RNA and RNA/DNA hybrid.

According to a preferred embodiment, said nucleic acid is double-stranded DNA or single-stranded RNA which at least encodes a protein product of interest which is expressed effectively in said stem cell of the brain.

Said protein product of interest is chosen from the group composed of pro-apoptotic or anti-apoptotic proteins, survival factors, differentiation factors, cytokines, lymphokines, interleukins, growth factors, transcription factors, killer proteins, recombinases, integrases, transposases, enzymes involved with nucleic acids, and "reporter" proteins.

Among the pro- or anti-apototic proteins which may or may not be involved in the mitochondrial pathway, mention should be made, in a nonexhaustive manner, besides the proteins of the Bcl2 family (such as $BclX_L$, $BCLX_S$, $Bcl_w$, Bid, Bax, Bak), the proteins IAP, SMAC and Diablo. Preferably, said protein product of interest is the BcLX$_L$ protein.

The interleukines, cytokines and lymphopkines are chosen from a group preferably composed of interleukines Il-1, Il-2, Il-3, Il-4, Il-5, Il-6, Il-7, Il-8, Il-0, Il-10, Il-11, Il-12, Il-13, Il-14, Il-15, Il-16, Il-17 and Il-18, and interferons α-IFN, β-IFN and γ-IFN.

The growth factors are preferably epithelial growth factor (EGF), fibroblast growth factor (FGF, and bFGF, basic fibroblast growth factor), platelet-derived growth factor (PGDF), nerve growth factor (NGF), brain-derived neurotrophic factor (BDNF), and glial-derived growth factor (GDGF); mention should also be made of the colony stimulating factors, such as G-CSF, GM-CSF, or M-CSF, and erythropoietine. Mention should also be made of the growth factors which interact, by inhibiting, with nucleic transcription factors such as NF-Kβ.

Among the transcription factors, mention should be made of the transcription factors which make it possible to direct the expression of a gene in a particular cell type or at a given moment of brain cell differentiation, and mention should be made of the transcription factors involved in the differentiation of neuronal cells, such as the neurogenins, and glial cells, such as GCM (glial cell missing). Among these factors, mention should be made, in a nonexhaustive manner, of the Dlx, Otx, Emx and Hox families.

It may also be an advantage to target the expression of killer proteins in the stem cells of the brain, or in cells of the brain in an active division phase. In this case, it is advantageous to use a nucleic acid molecule which encodes a protein product of interest chosen from killer proteins; among the killer proteins, mention should be made of kinases, and preferably thymidine kinase, and the pro-apoptotic proteins; the term "pro-apoptotic proteins" is intended to denote the proteins which are involved in apoptose or promote apotose. Among the pro-apoptotic proteins, mention should be made of the BIK (Bcl2-interacting protein), BAX (Oltvai et al., 1993), BAK (Chittenden et al., 1995; Kiefer el al., 1995) and BID (BH3-interacting domain death agonist) (Wang et al., 1996) proteins. Among the pro-apoptotic proteins, mention should also be made of caspases, the AIF (apoptosis-inducing factor) protein (Susin el al., 1999) and the proteins of the tumor necrosis factor (TNF) family, and more particularly TNF itself (Old 1985) and the FASL (FAS-ligand) protein (Takahashi et al., 1994).

The term "recombinase protein" is intended to denote the recombinases of the integrases family which catalyze the excision, insertion, inversion or translocation of DNA fragments at specific sites of recognition for said recombinases (Sternberg et al., 1986; Sauer, et al., 1990; Barbonis et al., 1993; Kilby et al., 1993, Sauer, 1994, Denisen et al., 1995). These recombinases are active in animal cells (Sauer, 1994). The recombinase protein of the invention is preferably selected from the group of site-specific recombinases composed of the bacteriophage P1 Cre recombinase, the *Saccharomyces cerevisiae* FLP recombinase, the *Zygosaccharomyces rouxii* pSRI recombinase R, the *Kluyveromyces drosophilarium* pKD1 recombinase A, the *Kluyveromyces waltii* pKW1 recombinase A, the λ Int integrase, and the recombinase of the Mu phage GIN recombination system, or a variant thereof.

According to a preferred embodiment, the recombinase is the Cre (cyclization recombination) recombinase, which is a 38 KDa integrase of the bacteriophage P1 which catalyzes, in the absence of cofactors, recombination between two DNA sequences of 34 base pairs called "loxP site" (Sauer et al., 1990). The position on one or more DNA molecules and the orientation of loxP sites compared to one another determine the type of function of the Cre recombinase: an excision, insertion, inversion or translocation. Thus, the recombinase activity of Cre is an inversion when two loxP sites are head-to-tail on the same DNA fragment, and an excision when the loxP sites are in direct repetition on the same DNA fragment. The activity of the recombinase is an insertion when a loxP site is present on a DNA fragment, it being possible for a DNA molecule such as a plasmid containing a loxP site to be inserted at said loxP site. The Cre recombinase can also induce a translocation between two chromosomes, on condition that a loxP site is present on each one of them (Babinet, 1995). More generally, the Cre recombinase is therefore capable of catalyzing recombination between one or more different DNA molecules, on condition that they carry loxP sites. One of the objects of the present invention is therefore to use a nucleic acid/PEI complex for the targeting of stem cells, so as to introduce therein a vector expressing the site-specific recombinase, in which the site-specific recombinase, encoded by said nucleic acid, is expressed in order to catalyze the recombination of a fragment of DNA of the genome of said stem cell of the brain.

Among the transposases, mention should be made of the patented "transposon sleeping beauty" system (Kay et al., 2000) or any other system for introducing a plasmid with IR ("inverted repeat") sequences framing a nucleic acid sequence of interest, with another expression vector plasmid for a transposase specific for the IR sequences, by cotransfection.

Such transposases catalyze the transposition and/or the integration of a DNA sequence of interest into the genome of said stem cell, it being possible for this DNA sequence of interest to be introduced into said cell using the complex according to the invention.

Among the enzymes involved with nucleic acids, mention should be made of the enzymes involved with DNA, such as restriction enzymes, DNA polymerases or ligases, and the enzymes involved with RNA, such as DNA-dependant RNA polymerases or reverse transcriptases.

According to another embodiment of the invention, the nucleic acid molecule is an antisense RNA, a double-stranded RNA, or a DNA/RNA chimera. Such RNA molecules can be used to inhibit the expression of a protein product of interest.

It is evident that the compound according to the invention has many uses, depending on the nature of the DNA sequence. These many uses can be easily envisioned by those skilled in the art and cannot be mentioned exhaustively. However, it should be underlined that the protein of interest encoded by the nucleic acid, or the antisense RNA, can be used to modify the expression of at least one cellular or mitochondrial gene, i.e. to decrease, to increase, to modulate or to destroy the expression of said gene. The protein of interest can also be used to induce the expression of at least one gene of interest; in this case, the protein of interest is preferably a transcription factor.

According to another embodiment, the protein of interest is a "reporter" protein. Among the "reporter" proteins, mention should be made, in a nonexhaustive manner, of luciferase, green fluorescent protein (GFP), β-galactosidase (β-gal) and chloramphenicol acetyltransferase (CAT). Such "reporter" protein can be used to follow the evolution of the stem cells in the brain. One of the objects of the present invention is therefore to use the complex according to the invention for targeting stem cells of the brain, in which the nucleic acid encodes a "reporter" protein or constitutes a signal-generating marker in order to enable detection, localization and imaging of stem cells of the brain.

The nucleic acid constitutes a signal-generating marker when said nucleic acid is labeled with radioactive isotopes or with non isotopic entities. The non isotopic entities can be selected from enzymes, dyes, haptenes, luminescent agents, such as radio luminescent, chemiluminescent, bioluminescent, fluorescent or phosphorescent agents, and ligands, such as biotin, avidin, streptavidin or digoxigenin. The methods for revealing and detecting these markers are well known to those skilled in the art.

The present invention therefore provides an effective system which allows the active or passive transport of the nucleic acid molecule across the cytoplasmic membrane, transport to the nucleus, entry into the nucleus and maintenance of this molecule in the functional state in the nucleus. The persistence of the expression of the protein product encoded by the DNA molecule is obtained either by stable integration of the DNA molecule into the chromosomal DNA of the target cell, or by maintenance of the DNA molecule in the episomal form. For certain uses, transient expression with a plasmid in the episomal form may be sufficient to obtain the desired results.

A subject of the invention is also a method of producing an animal, with the exception of humans, in which at least one stem cell of the brain has undergone at least one event of site-specific recombination targeted to a DNA sequence of interest, characterized in that said method comprises the steps of:
  (a) obtaining a totipotent embryonic stem (ES) cell modified by insertion of (a) recognition site(s) for said site-specific recombinase protein into said DNA sequence(s) of interest, located in one or more chromosomes, by homologous recombination;
  (b) introducing said modified totipotent embryonic stem cell into an embryo of said organism;
  (c) selecting the individuals having integrated the genetic modification into the germinal cells;
  (d) developing said animal;
  (e) introducing at least one said nucleic acid/cationic polymer complex into the brain of said animal obtained in step (d) close to or into the ventricular stem cells, said nucleic acid at least encoding a recombinase protein capable of catalyzing the recombination between said recognition sequences for said recombinase;
  (f) expressing said recombinase protein in said cell.

According to a particular embodiment, at least a second nucleic acid/cationic polymer complex can be introduced into the brain of said animal in step (e), and said second nucleic acid is a gene of interest as previously described. Such an embodiment makes it possible to target the integration of a DNA molecule of interest into the cellular genome.

The invention also relates to another method of producing an animal, with the exception of humans, in which at least one cell of the brain, with a high mitotic capacity, preferably a stem cell of the brain, has undergone at least one event of site-specific recombination targeted to a DNA sequence of interest, characterized in that said method comprises the steps of:
  a) obtaining a somatic cell modified by insertion of (a) recognition site(s) for said recombinase protein into said DNA sequence(s) of interest, located in one or more chromosome(s), by homologous recombination;
  b) transferring the nucleus of said modified somatic cell into the cytoplasm of an enucleated recipient oocyte (nuclear cloning);
  c) developing the embryo obtained in step b);
  d) introducing at least one said nucleic acid/cationic polymer complex into the brain of said animal obtained in step c) close to or into the ventricular stem cells, said nucleic acid at least encoding a recombinase protein capable of catalyzing the recombination between said recognition sequences for said recombinase;
  e) expressing said recombinase protein.

The nuclear cloning technologies are known to those skilled in the art; mention should be made of those which are the subject of patent applications WO 95 17500, WO 97 07668, WO 97 07669, WO 98 30683, WO 99 01163 and WO 99 31743.

The insertion of the specific recognition sites, in particular of the LoxP sites for the Cre recombinase, in the DNA sequence of interest is preferably carried out by homologous recombination; according to another embodiment, it may be carried out randomly.

The invention also relates to a method of producing an animal intended for the screening of compounds intended to modify the evolution of the stem cells of the brain, characterized in that it comprises the following steps:
  (a) Preparation of the nucleic acid/cationic polymer complex;
  (b) Introduction of said complex into the brain of said animal close to or into the ventricular stem cells;
  (c) Penetration of said nucleic acid into said stem cells.

According to a preferred embodiment, said complex is introduced by interventricular stereotactic injection; the nucleic acid of said complex is preferably double-stranded DNA which integrates into the genome of the stem cells of the brain. According to another embodiment, said nucleic acid is a double-stranded nucleic acid which is present in the episomal state; in this case, the nucleic acid sequence may be capable of self-replicating and possibly able to be amplified extra chromosomally.

The nucleic acid of the complex according to the invention is introduced in the form of an expression vector. The term "vector" will be intended to denote a nucleotide sequence capable of being transcribed. The vector may in particular be a bacteria plasmid DNA, a cosmid, phage DNA, viral DNA, in particular retrovirus or adeno-associated virus DNA, a mini chromosome (BAC, YAC, HAC, etc.,) or a transposon. The vector, or one of its fragments, comprises at least one gene encoding a protein of interest or an antisense RNA, and a promoter or expression elements for directing and controlling the expression of said protein of interest or of said antisense RNA in at least one stem cell of the brain of said organism. The expression vector also comprises translation initiation and termination signals, and also suitable regions for regulating transcription. These various control signals are chosen as a function of the cell type.

The term "expression elements" is intended to denote all the DNA sequences involved in regulating gene expression, i.e. the minimum promoter sequence, the upstream sequences, the activating sequences (enhancers), optionally the inhibiting sequences (silencers) and the insulator sequences.

Preferably, the gene of interest is placed under the control of tissue-specific or cell-specific or ubiquitous expression elements.

The tissue-specific expression elements or tissue-specific promoters are chosen from the promoters which make it possible to obtain specific, and preferably strong, expression in one or more cell(s), tissue(s) and/or cell type(s) of the brain, and in particular in the neurons, astrocytes, oligodendrocytes and/or glial cells. These promoters may or may not be heterologous to the organism and may or may not be naturally present in the genome of the organism. By way of non limiting example of tissue-specific promoters, mention may be made of the oligodendrocyte-specific promoter of the myelin basic protein (MBP) gene and the neuron-specific promoter of the gene encoding neuron specific enolase (NSE).

According to another embodiment, the expression elements consist of inducible promoters such as, for example, the tetracycline system (Goossen et al., 1992).

Finally, an animal which can be obtained using one of the methods according to the invention is also within the scope of the invention.

The invention also relates to a method of screening compounds intended to modify the evolution of stem cells of the brain, characterized in that it comprises the steps:
(a) Bringing an animal which can be obtained using the method according to the invention into contact with said compound to be screened,
(b) Analyzing the evolution of the stem cells of the brain.

The compound which can be obtained using the above method also falls within the scope of the present invention. Such a compound can be used to prepare a medicinal product intended for the treatment of neurodegenerative and/or demyelinating diseases.

Other characteristics and advantages of the present invention will be demonstrated more clearly on reading the following examples.

In these examples, reference will be made to the following figures:

The patent or application file contains at least one drawing executed in color. Copies of this patent or patent application publication with color drawing(s) will be provided by the Office upon request and payment of the necessary fee.

FIG. 1 Distribution and morphology of the cells expressing β-galactosidase after intraventricular injection of CMV-LacZ/PEI complexes One week after intraventricular injection into an adult mouse, 100 µm of vibratome sections were used to reveal the sites of expression of the β-galactosidase (black labeling).

Panel A shows a composite view of the distribution of positive cells observed in six independent experiments. Transfected cells are particularly abundant in the striatal part of the lateral ventricles, where they can be found in the anterior and posterior subventricular zones (SVZ) (C). Groups of positive cells (black labeling) are also present in the region of the hippocampus (hp), of the posterior lateral ventricle (C, C'), and along the third ventricle (D). In the SVZ, the positive cells (black labeling) either exhibit the typical morphology of subependymal astrocytes (E, F) or are present as a group of small round cells (G, H). In the third ventricle, most of the cells project long outgrowths from the ependymal layer (P). Scale: (B-C), 200 µm; (C' and H), 40 µm; (D), 100 µm; (E-G and P), 20 µm; ep, ependyma; hip, hippocampus; lu, lateral ventricle; svz, subventricular zone.

Figure 2:
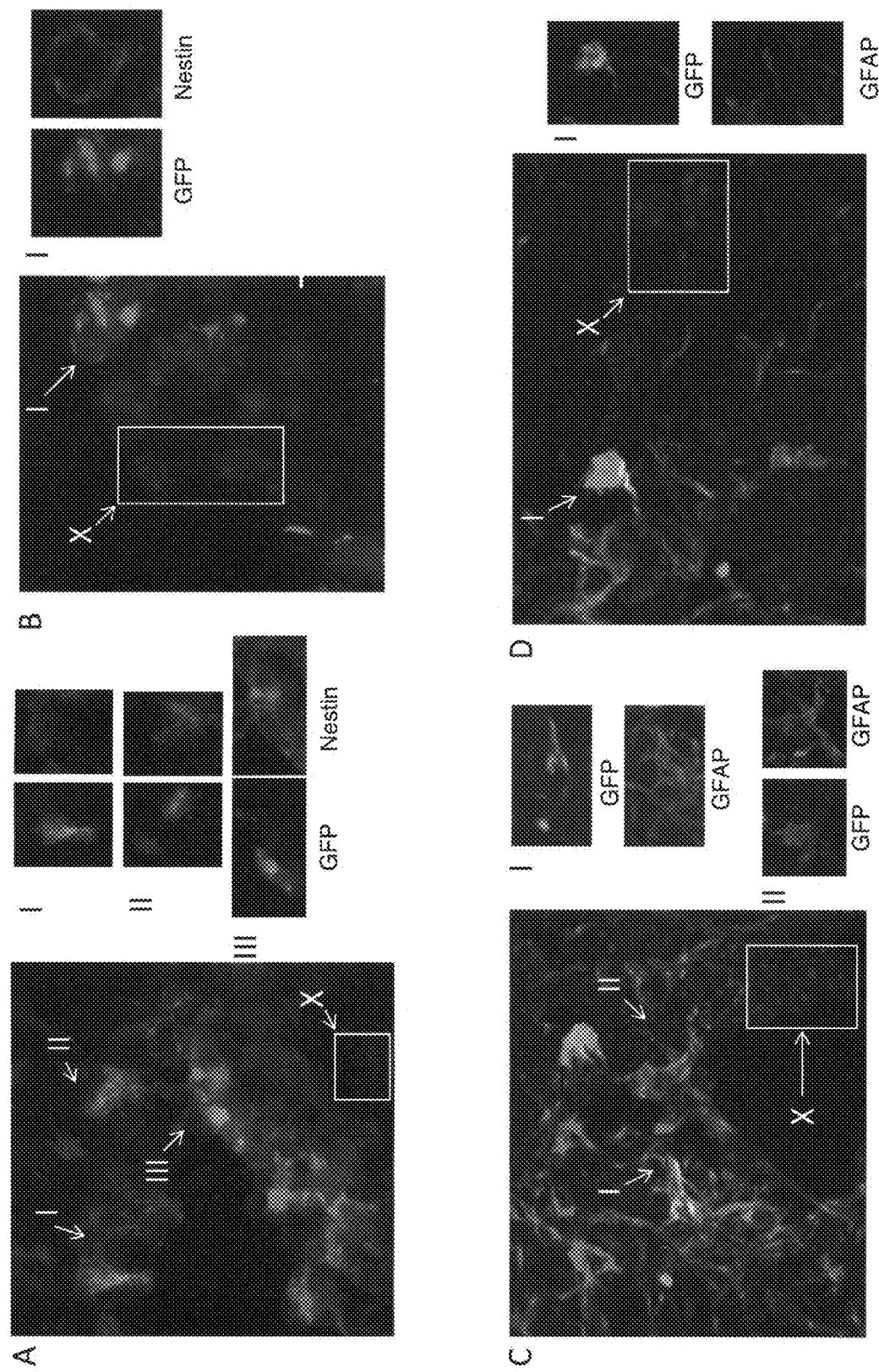

FIG. 2: Expression of GFAP and of Nestin in the transfected cells

Brain sections (8 µm) from an adult mouse transfected, one week before being sacrificed, with CMV-LacZ/PEI complexes.

The sections were double-stained in order to detect the expression of Lac Z and of GFAP (A, B) or of Lac Z and of Nestin (C, D). The cells positive for β-galactosidase are only present in regions of expression of GFAP and Nestin. At a higher magnification, it appears that, at least in some cells, GFAP (B) or Nestin (D) are coexpressed with the LacZ reporter gene. Scale: (A, C), 40 µm; (B, D), 12 µm.

Figure 3:
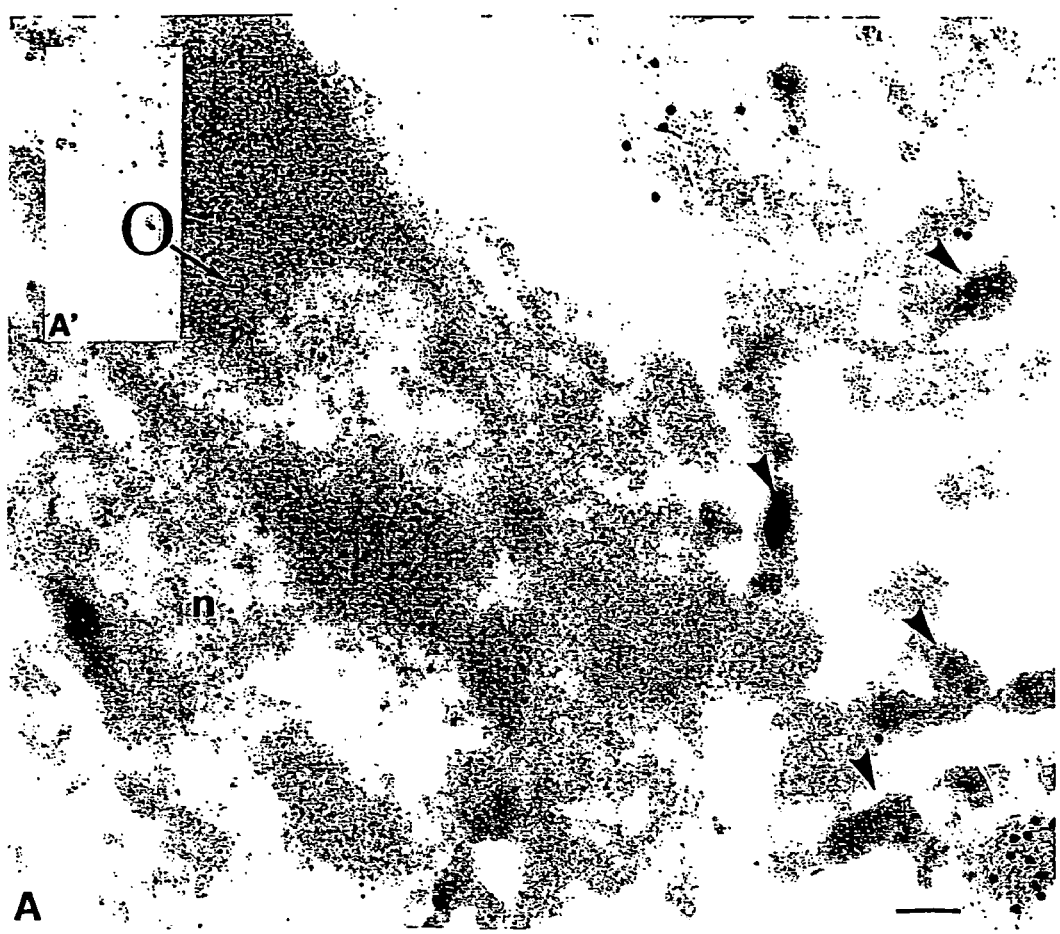

FIG. 3: Ultrastructural analysis of the SVZ one week after intravectricular injection of CMV-LacZ/PEI complex A') Semi-thin section of the SVZ region of the brain of an adult mouse treated with BrdU present in the drinking water and then transfected with CMV-LacZ/PEI complexes four days before being sacrificed.

The sections are stained with BluoGal in order to reveal the expression of the transgene (cell circled in black).

A) Ultra-thin adjacent section immunostained for the detection of BrdU (10 nm colloidal gold) and of GFAP (20 nm colloidal gold). The BrdU is exclusively located in the nucleus (n), whereas the GFAP is associated with regions rich in fibers of the cytoskeleton (white arrows). The electron-dense BluoGal precipitates are indicated by arrowheads. This image shows transfection of the DNA/PEI complexes into the subventricular astrocytes which have divided. Scale: 100 µm.

Figure 4:
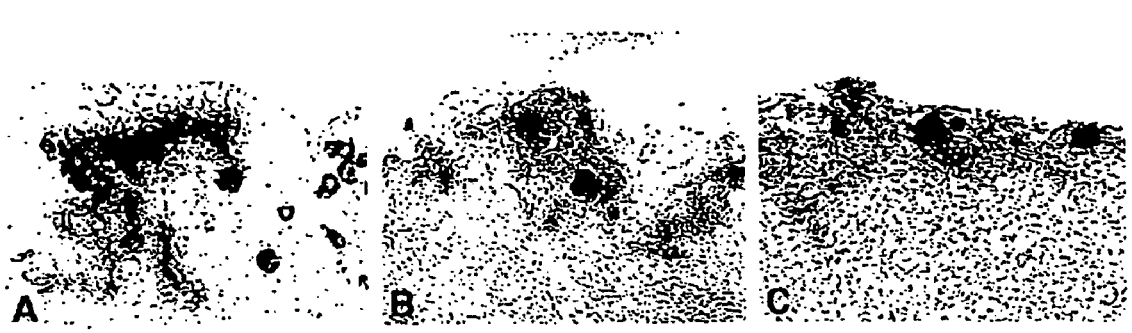

FIG. 4: Transfection of slowly and rapidly dividing cells in the SVZ, with the DNA/PEI complexes Mice were treated with BrdU according to various protocols in order to identify the slowly and rapidly dividing cells of the SVZ.

In A, the mice are treated with BrdU continually for three weeks before being transfected and then sacrificed; in this case, all the dividing cells incorporate the BrdU.

In B, the mice are treated for eighteen days with BrdU, and then with a three-day flush period without BrdU treatment, before being analyzed. In this case, the slowly dividing cells are labeled intensely with the anti-BrdU antibodies, whereas the rapidly dividing cells exhibit a less intense labeling of the BrdU signal since they continue to divide during the flush period.

Finally, in C, the mice only received a four-day treatment with BrdU; in this case, the rapidly dividing neuroblasts are positively labeled with BrdU. In all the cases, the transduction of the cells is carried out in zones of intense cell proliferation.

Figure 5:
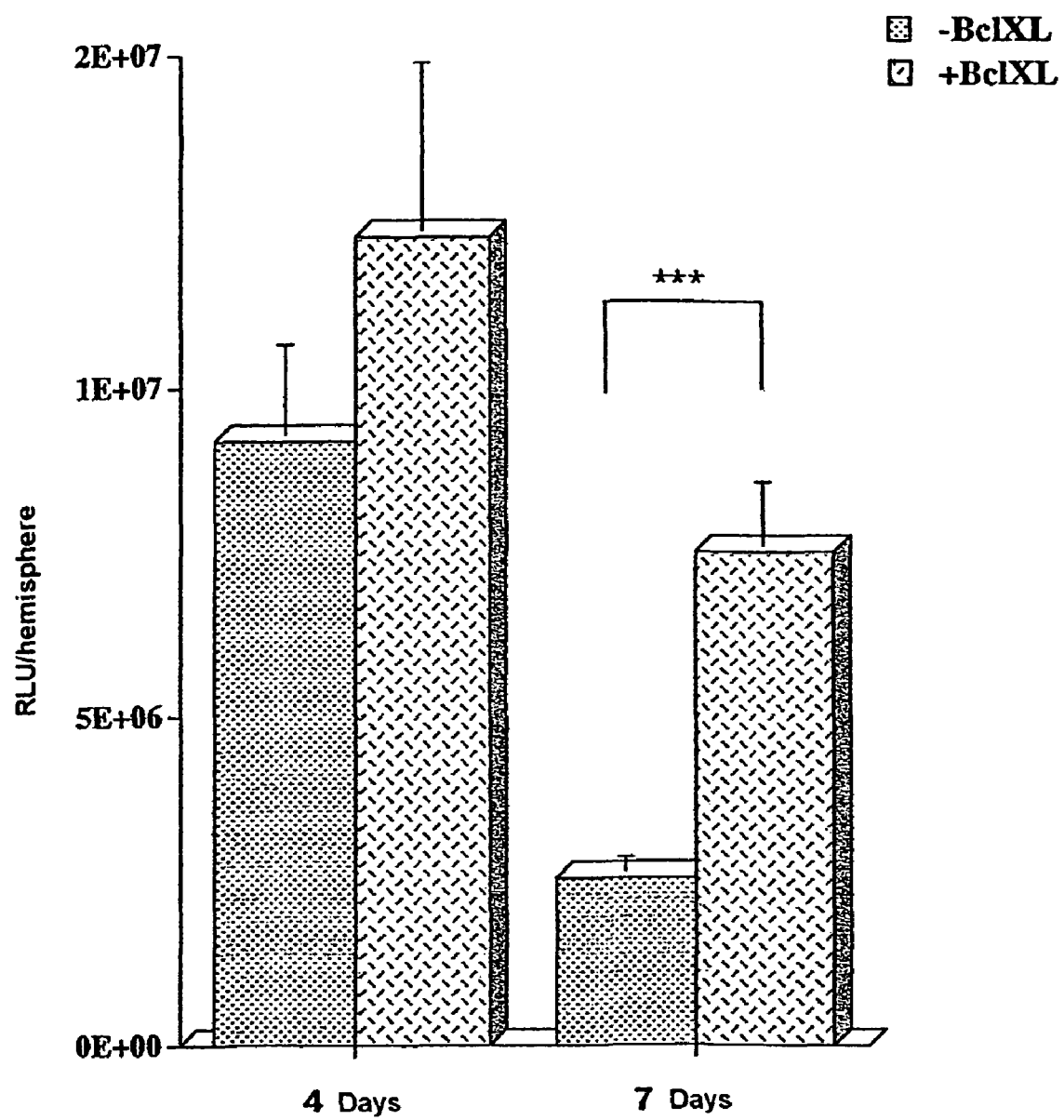

FIG. 5: The transfection of Bcl-$X_L$ in th SVZ prolongs the survival of the transfected cells The anti-apoptotic gene Bcl-$X_L$ was cotransfected with the luciferase reporter gene in order to quantify cell viability. A significant increase in expression of luciferase above the level of expression of the control cells was observed one week after transfection. In the presence of Bcl-$X_L$, there is no decrease in the expression of luciferase throughout the duration of the experiment (RLU=relative light unit; 0E+00=0; 5E+06=5.10$^6$; IE+07=10$^7$; 2E-07=2.10$^7$).

Figure 6:
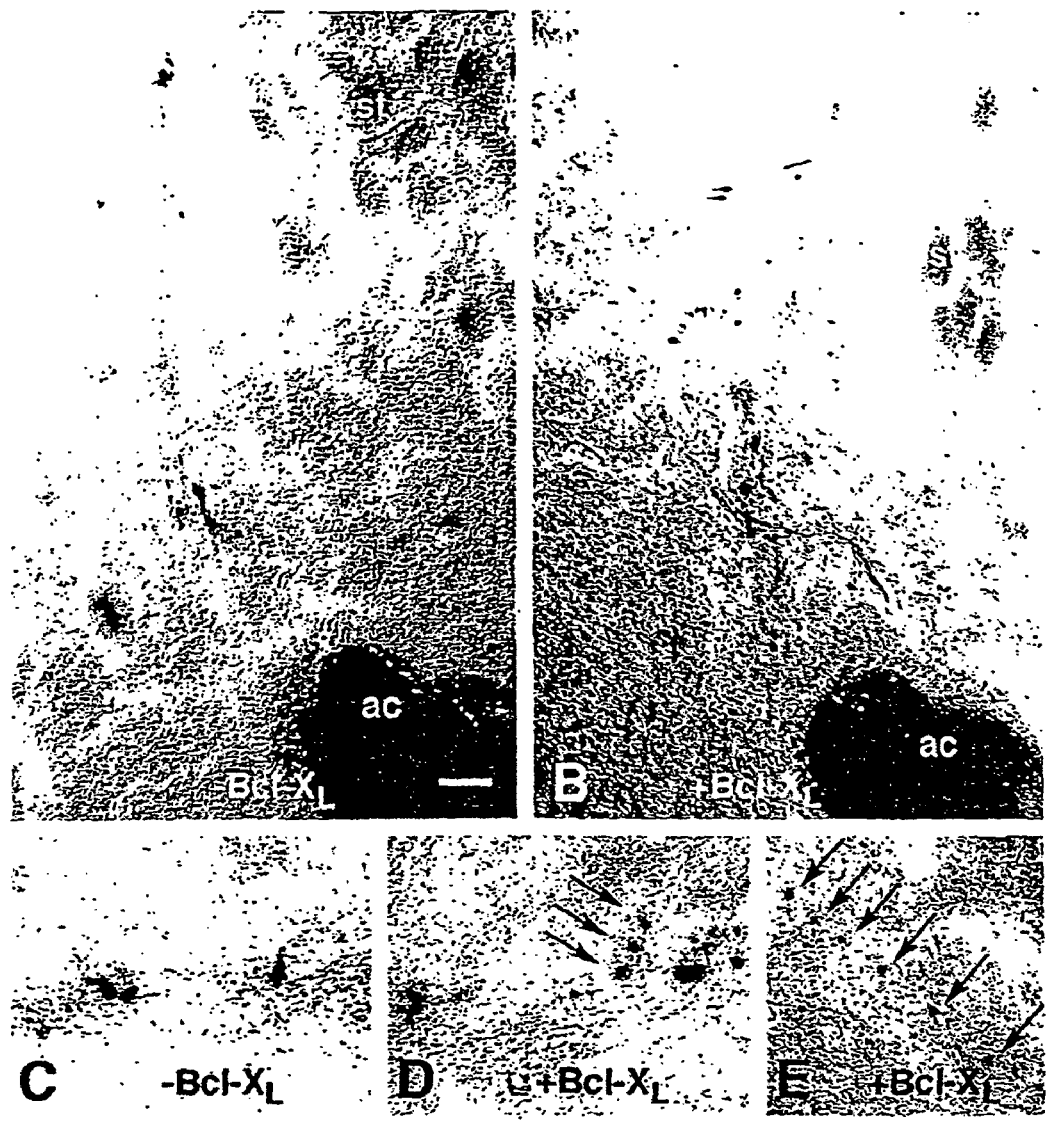

FIG. 6: The expression of the anti-apoptotic gene BclX$_L$, in the sub-ventricular cells, makes it possible to observe a modification of the expression profile of the LacZ reporter gene, one week after injection Cotransfection of the vector CMV-lacZ with a control plasmid (A, C) or a plasmid carrying the Bcl-$X_L$ gene (B, D and E). With Bcl-$X_L$, the number of cells expressing the transgene at one week post-injection is greater. Among these cells transfected with the anti-apoptotic gene which survive, many groups of cells are observed which appear to have migrated or which may be derived from one another. Scale: (A, B) 100 µm; (C to E) 40 µm.

Figure 7:
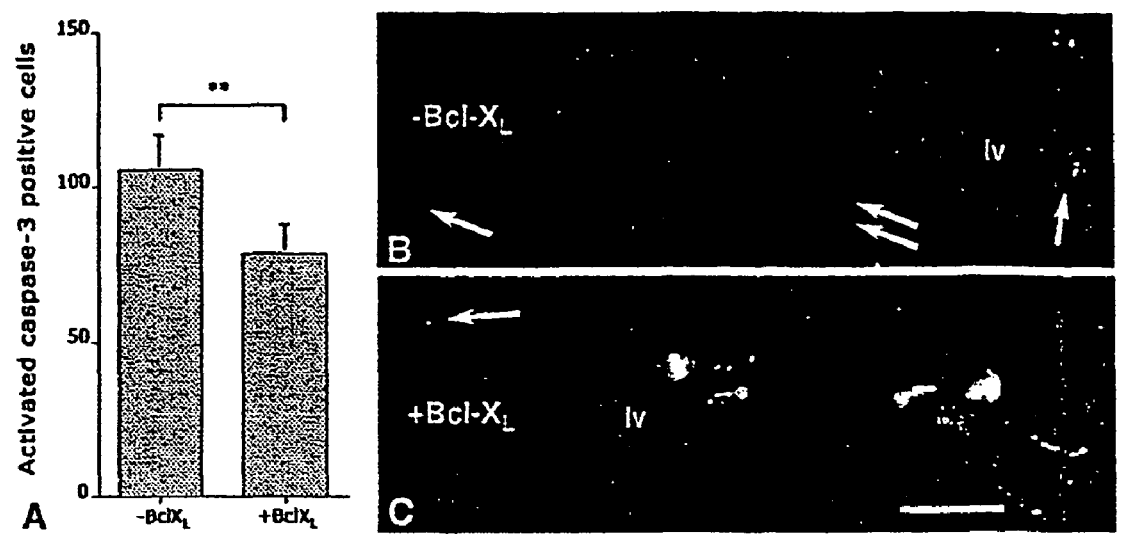

FIG. 7: The overexpression of Bcl-$X_L$ decreases the number of cells immunopositive for the activated form of caspase-3 (A, B, C)

The plasmid CMV-GFP was cotransfected by intraventricular injection with a control plasmid or with the plasmid CMV-Bcl-$X_L$. Immunodetection of the activated form of caspase-3 was carried out on cryostat sections (10 µm). The immunopositive cells were counted from 0.8 to 1.2 mm of the part anterior to bregma for each animal. The number of positive cells is significantly decreased in the animals transfected with CMV-Bcl-$X_L$ compared to the injected or non injected control animals (A) or non injected control animals (see text).

The means±SD (SD: standard derivation) are given, with n≧4 animals per group. Observation by immunofluorescence of the cells positive for the activated form of caspase-3 positive in the brains transfected with CMV-GFP cotransfected with a control plasmid (B) or with CMV-Bcl-$X_L$ (C). The cells immunopositive for the activated form of caspase-3 (white arrows) are often present in the form of doublets in the control (B). In the presence of Bcl-$X_L$ (C), a decrease in the number of cells positive for the activated form of caspase-3 is observed, whereas the number of cells expressing the GFP transgene is increased. Iv, lateral ventricle. Bar: (B-C), 40 µm.

Figure 8:

FIG. 8: Lac Z expression in the brain of transgenic mice 3 months after recombination induced by transfection of pCMV-CRE complexed with PEI CMV-CRE is transfected, by a single intraventricular injection, into R26R mice and the lacZ expression resulting from recombination is observed 3 months after injection. Many cells expressing lacZ can be detected at distances of 250 µm from the subventricular zone. Iv, lateral ventricle. Bar: 50 µm.

EXAMPLES

1) Materials and Methods 1.1) Preparation of the Plasmids, Formulation of the DNA/PEI Complexes, and Stereotactic Injection The purified DNA, without endotoxine, is prepared using affinity columns (Genomed, Research Triangle Park, N.C., USA). The DNA is washed with 70% ethanol, resuspended in a tris-EDTA buffer, and stored at 4° C.

In order to follow the expression of the exogenous genes after injection into the mouse brain, the inventors used plasmids comprising either the coding sequence of β-galactosidase, for the histological study, or the coding sequence of firefly (*Photinus pyralis*) luciferase for the biochemical quantification of the expression of the transgene. The two genes are under the control of the cytomeglaovirus (CMV) promoter obtained from Vical Inc., San Diego, Calif., USA.

The inventors constructed the expression vector pCMV-Bcl-$X_L$, containing the gene encoding the chicken Bcl-$X_L$ protein under the control of the CMV promoter, in the plasmid pcDNA$_3$ (Invitrogen, Carlsbad, Calif., USA).

The plasmid DNA is diluted to the desired concentration in 5% glucose and is then complexed with the appropriate amount of linear 22 Kd PEI (ratio of 6 between the protonatable amines of the PEI and the phosphates of the DNA, given that 1 µl of 1M PEI represents 1000 nmol of protonatable amines and 1 µg of DNA represents 3 nmol of phosphates).

The solution of complexes is injected into the lateral ventricle (0.2 mm posterior to the bregma line, 1.1 mm laterally from the saggital suture and 2.2 mm deep relative to the surface of the cranium) of mice approximately two months old, anesthetized with pentobarbital (Sanofi 65 mg/kg). The needle for the injection is left in place for at least 10 minutes.

One microgram of each plasmid complexed with the PEI is sufficient to obtain a level of expression necessary for the implementation of the invention.

All the procedures involving animals were carried out while respecting the recommendations established by the national and European institutions.

1.2) Proliferation Study

The BrdU is administered in the drinking water (1 mg/ml Fluka) for three weeks, or by intraperitoneal injection (150 mg/kg).

1.3) Histological Study

The mice are sacrificed and the brains are dissected and post-fixed in 2% paraformaldehyde. The β-galactosidase reaction is carried out on vibratome sections (50 µm) by immersion in an X-Gal solution at 30° C. for five hours (0.4 mg/ml X-gal, Genaxis, Montigny le Bretonneux, France). After staining, the sections are mounted on gelatinized slides.

The BrdU labeling is observed on paraffin sections (5 µm) with an anti-BrdU mouse monoclonal antibody (Dako) at a 1:50 dilution in PBS with 1% of bovine serum albumine (BSA). The primary antibody is revealed with an anti-mouse antibody biotinylated before its application to prevent the endogenous reactivity (Dako ARK kit). The antigenic sites are unmasked with two microwave cycles (5 min. at 750 W in a 10 mMol citrate buffer). The staining is then completed by incubation with streptavidin-coupled peroxidase and the reaction is carried out in the presence of diaminobenzidine as chromogenic substrate (Dako ARK kit).

The anti-GFAP monoclonal primary antibody (Boehringer) is used at 1:400 on paraffin sections and detected as above with the peroxidase-coupled revelation system (Dako ARK kit).

The anti-nestin monoclonal primary antibody (Chemicon) is used at 1:500 on cryostat sections (10 µm) and detected as above with the peroxidase-coupled revelation system (Dako ARK kit).

1.4) Electron Microscopy Study

The mice treated with BrdU for three weeks are injected with the LacZ expression vector complex with the PEI, sacrificed four days post-injection, and perfused with 3% paraformaldehyde at 0.2% glutaraldehyde. The brains are detected and post-fixed. Sections are cut on a vibratome (90 µm) and stained with a solution of BluoGal substrate (Gibco) for five hours at 30° C. The sections are rinsed with a cacodylate buffer (0.1M, pH 7.2; Prolabo) and the aldehyde groups are blocked with 50 mMol $NH_4Cl$ (Merck). After a rinse with a veronal buffer (pH 6), the sections are contrasted with a 0.5% uranyle acetate solution (Fluka) in the same buffer, and then dehydrated in a series of baths with an increasing ethanol gradient. The sections are finally embedded in an LRWhite resin (Sigma). In order to select the regions of expression of the transgene, semi-thin sections of 1 µm are cut from the vibratome sections, so as to subsequently collect the adjacent ultra-thin (100 nm) sections of nickel grids (200 mesh) in order to perform the immunohistology.

The immunodetection of BrdU and of GFAP are carried out on the same face of the grid bearing the tissue. The sections are incubated for thirty minutes in a saturating buffer (Sörensen buffer with 1% bovine serum albumine (BSA)). The primary antibodies, rabbit anti-GFAP polyclonal at 1:750 (Dako) and mouse anti-BrdU monoclonal at 1:25 (Caltag), are applied to the tissue in the Sörensen buffer containing 0.2% of BSA and 0.025% of Tween 20 (overnight at 4° C.). After washing, the secondary antibodies, goat anti-rabbit IgG and goat anti-mouse IgG coupled to gold beads of respectively 20 and 10 nm, are applied to the specimens at a dilution of 1:50. The counter-staining corresponds to a fifteen-minute treatment in 4% uranyle acetate. The sections are observed at 75 kV with a Hitachi H7100 electron microscope.

1.5) Luciferase Quantification

The activity of the transgene is measured on the homogenized tissue as specified in Lemkine et al., (1999).

1.6) Mapping of the Brain and Cell Counting

In order to obtain a representation of the location of the cells expressing the transgene on successive coronal sections (from 1.3 mm anterior to 2.7 mm posterior relative to the bregma line), the inventors selected the corresponding sections on the vibratome (100 μm). The blue cells are counted on six different brains in order to calculate the mean number of cells for each site of expression of the transgene. Regions representative of the sections are chosen to be drawn on each of the coronal representations making up the mapping.

1.7) Murine line R26R

The mouse line R26R exhibits constitutive n-Gal expression in all the cells where a recombination with the CRE recombinase takes place (Soriano, 1999). Thus, this offers an ideal system for following, in the long term, the expression of a reporter gene being expressed subsequent to the transfection of the CRE gene by gene transfer using PEI.

1.8) Anti-Caspase-3 Antibody

To detect the caspase-3 in its active form, the inventors used a rabbit polyclonal antibody, CM1, which specifically recognizes the p18 subunit of cleaved caspase-3 (given by the company IDUN Pharmaceuticals, Inc. to Dr. G. Levi).

2) Results 2.1) The Overexpression of Bcl-$X_L$ Decreases the Number of Cells Immunopositive for the Activated Form of Caspase-3

Caspase-3 is an effectual caspase (Budihardjo et al., 1999) which acts downstream of Bcl-$X_L$ in post-mitotic neurons and which independently regulates apoptoses in the neural stem cells of the subventricular zone in newborn mice (Roth et al., 2000). The inhibitory action of the Bcl-$X_L$ on programmed cell death should be reflected by a decrease in the number of cells expressing active caspase-3 in the subventricular zone. To verify this hypothesis, the inventors used an antibody which detects the activated form of caspase-3 (Roth et al., 2000) and compared the numbers of immunopositive cells in the brains of non-transfected mice and mice transfected with or without Bcl-$X_L$. As shown by the results (FIG. 7), overexpression of the anti-apoptotic protein decreases the number of cells positive for activated caspase-3 in the subventricular zone, while the number of cells expressing the GFP reporter transgene increases. The quantification shows 105±11 and 78±9 cells (means±S.D.; n=4) respectively in the control brains and those injected with Bcl-XL ($p<0.01$) in series of an anatomically equivalent sections. The activation of caspase-3 is not due to the transfection procedure since the number of positive cells is not significantly different between the non injected control animals (95±2 cells/brain) and those transfected with a control plasmid (105±11 cells/brain). These results demonstrate the effectiveness of the method for modifying the evolution of the targeted cells.

2.2) The Stable Expression of lacZ After Transfection of the Cre Recombinase Shows That the Progeny of the Transfected Cells is Capable of Migrating To analyze the destiny of the transfected cells, we used R26R transgenic mice (Soriano, 1999). In this model, the transfection and the expression of Cre recombinase produces a rearrangement of the lacZ gene, inducing the stable expression of lacZ in the transfected cells and their descendance. As shown in the figure, 3 months after intraventricular injection of CMV-CRE, many cells expressing lacZ are present in the brain of the treated mice. On most of the sections, the cells expressing lacZ are often located in the parenchyma at distances of 250 μm from the subventricular zone. These observations show that the cells derived from the transfected cell population possess a migratory capacity, which is a demonstrated property of the descendance of neural stem cells (Doetsch et al., 1996).

REFERENCES

Abdallah et al. (1996) Human Gen Therapy 7: 1947-1954.
Akli et al. (1993) Nature Genet. 3: 224-228.
Babinet, (1995) Medecine/Sciences 11: 1154-1157.
Bajocchi et al. (1993) Nature Genet. 3: 229-234.
Barba et al. (1994) Proc. Natl. Acad. Sci. USA 91: 4348-4352.
Barbonis et al. (1993) Nucleic Acids Res. 21: 2025-2029.
Behr et al. (1989) Proc. Natl. Acad. Sci. USA 86: 6982-6986.
Boussif et al. (1995) Proc. Natl. Acad. Sci. USA 92: 7297-7303.
Boviatsis et al. (1994) Hum. Gene Ther. 5: 183-191.
Budihardjo et al. (1999) Annu Rev Vell Dev Biol 15: 269-90.
Chambers et al. (1995) Proc. Natl. Acad. Sci. USA 92: 1411-1414.
Chiasson et al. (1999) J. Neurosci 19: 4462-4471.
Chittenden et al. (1995), Nature 374: 733-736.
Cotton et al. (1994) Gene Ther. 1: 239.
Culver et al. (1992) Science 256: 1550-1552.
Davidson et al. (1993) Nature Genet. 3: 219-223.
Davis et al. (1993) Hum. Gene Ther. 4: 151-159.
Denisen et al. (1995) Proc. Natl. Acad. Sci. USA 92: 7376-7380.
Doetsch et al. (1996) Proc. Natl. Acad. Sci. USA 93: 14895-900.
Doetsch et al. (1999) Cell. 97: 703-716.
Feigner et al. (1987) Proc. Natl. Acad. Sci. USA 84: 7413-7417.
Garcia et al. (1992) Science 258: 302-304.
Gavrieli et al. (1992) J. Cell. Biol 119: 493-501.
Goossen et al. (1992) Proc. Natl. Acad. Sci. USA 89: 5547-5551.
Goula et al. (1998) Gene Ther. 5: 712-717.
Johansson et al. (1999) Cell 96: 25.
Kaplitt et al. (1994) Nature Genet. 8: 148-153.
Kay et al. (2000) Nature Genet. 24: 257-261.
Kesari et al. (1995) Lab. Invest. 73: 636-648.
Kiefer et al. 1995, Nature 734: 736-739.
Kilby et al. (1993) TIG 9: 413-421.
La Gal La Salle et al. (1993) Science 259: 988-990.
Lemkine et al. (1999) Journal of Drug Targeting 4: 305-312.
McKay et al. (1997) Science 276: 66-71.
Naldini et al. (1996) Science 272: 263-267.
Old (1985) Science 230: 630-632.
Oltvai et al. (1993), Cell 74: 609-61.
Oupicky et al. (2000) J. Control release 65: 149-171.
Pakzaban et al. (1994) Hum. Gene Ther. 5: 987-995.
Planck et al. (1999) Hum. Gen. Ther. 10: 319-332.
Read et al. (2000) Evr. J. Pharm. Sci 10: 169-177.
Roth et al. (2000) Proc. Natl. Acad. Sci. USA 97: 466-71.
Sachs et al. (1997) FASEB J. 11: 801-808.
Sauer et al. (1990) The New Biologist 2: 441-449.
Sauer (1994) Current Op. im Biotechnology 5: 521-527.
Snyder et. al. (1995) Nature 374: 367-370.
Soriano (199) Nat. Genet. 21: 70-1.
Sternberg et al. (1986) J. Mol. Biol. 187: 197-212.
Susin et al. 1999, Nature 397: 441-446.
Takahashi et al. 1994, Int. Immun. 6: 1567-1574.
Tang et al. (1996) Bioconjug. Chem. 7: 703-714.
Wang et al. 1996, Genes Dev. 10: 2859-2869.
Wolfert et al. (1999) Bioconjug. Chem. 10: 993-1004.
Wood et al. (1994) Gene Ther. 1: 283-291.

The invention claimed is:

1. A method for specifically targeting stem cells of an adult brain of a rodent selected from the group consisting of mice and rats, comprising introducing into said adult brain by intraventricular injection close to ventricular stem cells of said adult brain a nucleic acid/cationic polymer complex composition,
   wherein when said adult brain is an adult mouse brain, the amount of said nucleic acid present in said composition is less than 0.75 µg and the volume of said composition does not exceed 5 µl and
   wherein when said adult brain is an adult rat brain, the amount of said nucleic acid present in said composition and the volume of said composition are a function of the volume of the cerebral ventricle of said adult rat brain and are determined proportionally to the amount and volume used to target the stem cells of an adult mouse.

2. The method as claimed in claim 1, wherein said composition is injected stereotactically for at least 10 minutes.

3. The method as claimed in claim 1, wherein said cationic polymer is polyethyleneimine.

4. The method as claimed in claim 1, wherein said adult brain is an adult mouse brain, the amount of said nucleic acid present in said composition being less than 0.5 µg.

5. The method as claimed in claim 1, wherein said adult brain is an adult rat brain.

6. The method as claimed in claim 1, wherein said composition is injected for following the differentiation of the stem cells of the brain.

7. The method as claimed in claim 1, wherein said composition is injected for increasing the survival of the stem cells of the brain.

8. The method as claimed in claim 1, wherein said nucleic acid is chosen from single-stranded DNA, double-stranded DNA, single-stranded RNA, double-stranded RNA or a RNA/DNA hybrid.

9. The method as claimed in claim 8, wherein said nucleic acid is double-stranded DNA or single-stranded RNA that encodes at least a protein product that is expressed effectively in said stem cells.

10. The method as claimed in claim 9, wherein said protein product is a cytokine, lymphokine, interleukine, transcription factor, survival factor, anti-apoptotic protein, pro-apoptotic protein, killer protein, growth factor, recombinase, integrase, transposase, enzyme involved with a nucleic acid, differentiation factor or reporter protein.

11. The method as claimed in claim 1, wherein said composition is injected for the detection, localization and imaging of the stem cells of the brain, and wherein said nucleic acid encodes a reporter protein.

12. The method as claimed in claim 11, wherein said reporter protein is luciferase, green fluorescence protein, β-galactosidase or chloramphenicol acetyltransferase.

13. A method for specifically targeting stem cells of an adult mouse brain comprising introducing into said adult brain by intraventricular injection close to ventricular stem cells of said adult brain, a nucleic acid/cationic polymer complex composition wherein the amount of said nucleic acid present in said composition is less than 1.5 µg and the volume of said composition does not exceed 5 µl.

* * * * *